United States Patent [19]

Berner et al.

[11] Patent Number: 4,582,862

[45] Date of Patent: Apr. 15, 1986

[54] KETONE WITH MORPHOLINO AND S-PHENYL GROUPS AS PHOTOINITIATOR IN PIGMENTED COATING

[75] Inventors: Godwin Berner, Rheinfelden; Rinaldo Hüsler, Basel; Rudolf Kirchmayr, Aesch, all of Switzerland

[73] Assignee: Ciba-Geigy Corporation, Ardsley, N.Y.

[21] Appl. No.: 468,531

[22] Filed: Feb. 22, 1983

[30] Foreign Application Priority Data

Feb. 26, 1982 [CH] Switzerland .................. 1196/82

[51] Int. Cl.$^4$ .......................... C08F 2/50; C08L 63/10
[52] U.S. Cl. ........................... 522/14; 522/17; 522/39; 522/36; 522/34; 522/81; 522/92; 522/101; 522/50; 522/53; 522/16
[58] Field of Search .................. 204/159.24

[56] References Cited

U.S. PATENT DOCUMENTS

| | | | |
|---|---|---|---|
| 2,759,970 | 8/1956 | Suter | 260/562 |
| 3,910,916 | 10/1975 | Protiva et al. | 260/268 |
| 4,124,722 | 11/1978 | Archer | 424/308 |
| 4,279,721 | 7/1981 | Kirchmayr et al. | 204/159.24 |
| 4,284,485 | 8/1981 | Berner | 204/159.24 |
| 4,315,807 | 2/1982 | Felder et al. | 204/159.24 |
| 4,318,791 | 3/1982 | Felder et al. | 204/159.24 |
| 4,321,118 | 3/1982 | Felder et al. | 204/159.24 |
| 4,351,708 | 9/1982 | Berner et al. | 204/159.24 |
| 4,390,453 | 6/1983 | Eichler et al. | 252/426 |

Primary Examiner—John C. Bleutge
Assistant Examiner—A. H. Koeckert
Attorney, Agent, or Firm—Harry Falber

[57] ABSTRACT

Compounds of the formula I, II or III

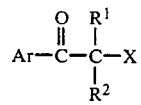

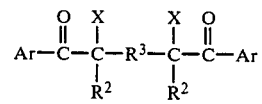

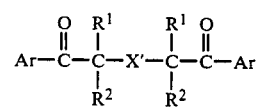

in which Ar is a sulfur-containing aromatic radical, $R^1$ and $R^2$ are a monovalent hydrocarbon radical which is substituted or unsubstituted or $R^1$ and $R^2$ together form alkylene, oxaalkylene or azaalkylene, $R^3$ is a direct bond or a divalent hydrocarbon radical, X is a monovalent amino group and X' is a divalent amino or diamino group, are excellent photoinitiators for the photocuring of colored, in particular pigmented, compositions containing an olefinically unsaturated, photopolymerizable binder.

5 Claims, No Drawings

KETONE WITH MORPHOLINO AND S-PHENYL GROUPS AS PHOTOINITIATOR IN PIGMENTED COATING

The invention relates to photocurable coloured compositions containing an olefinically unsaturated binder, a pigment or a dye and a specific photoinitiator. The photoinitiator is an aromatic-aliphatic ketone which contains, in the aromatic moiety, one or more specific sulfur-containing groups and contains, in the aliphatic moiety, a tertiary α-C atom on which an amino group is located.

It is known that photoinitiators are added before irradiation in order to accelerate the photocuring of coloured compositions, for example printing inks or paints. This makes it possible to cure such compositions in a very short time of irradiation sufficiently for their surface to be no longer tacky. Whereas there are a number of technically satisfactory photoinitiators for transparent coating compositions, the radiation curing of coloured compositions constitutes a problem particularly difficult to solve because of the presence of the light-absorbing pigments or dyes. In the case of printing inks there is also the requirement for extremely short curing times because of the high speed of modern printing machines. The requirements for photoinitiators for coloured compositions are therefore considerably higher than those for transparent photocurable compositions.

Photoinitiators which have hitherto been used in the art for the curing of such coloured compositions, for example printing inks or paints, are in most cases synergistic mixtures of ketonic photoinitiators with specific amines, for example a mixture of benzophenone with Michler's ketone (4,4'-bis-dimethylaminobenzophenone) or with alkyl p-dimethylaminobenzoates, or mixtures of thioxanthones with N-methyldiethanolamine. Ketone-amine mixtures of this type tend to undergo yellowing in light. This can manifest itself as early as the radiation curing, but at the latest when the cured layers are exposed to the prolonged action of light. Some of these compounds are sparingly soluble in the customary acrylic resin binders, tend to recrystallise and considerably shorten the storage life of the mixtures. Other compounds of this type, for example the alkanolamines, are soluble in water and therefore cannot be used for wet offset printing inks. Furthermore, the ketone-amine mixtures act in accordance with a bimolecular initiation mechanism which is controlled by diffusion and therefore takes place relatively slowly in systems of high viscosity.

Molecular combinations of aryl ketones and amines in which the amino group is located on a tertiary C atom in the α-position in relation to the carbonyl group have already been suggested as photoinitiators in European Patent Application, Publication No. 3002. However, the aminoketones described in this text have proved inferior as photoinitiators in clear lacquers to the corresponding hydroxyketones described in the same patent specification. The hydroxyketones described in this text are admittedly excellent initiators for transparent lacquers, but exhibit only a moderately good action in pigmented compositions, for example in printing inks.

It has been found, surprisingly, that aminoketones which carry at least one thioether or sulfoxide group on the aromatic nucleus exhibit an excellent initiator action in coloured compositions, particularly in printing inks, and do not have the disadvantages of the ketone-amine mixtures or have these disadvantages to a considerably smaller extent.

The invention relates, therefore, to photocurable coloured compositions containing:
(a) an olefinically unsaturated, photopolymerisable binder,
(b) a pigment or a dye and
(c) as the photoinitiator, at least one compound of the formulae I, II or III

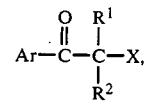

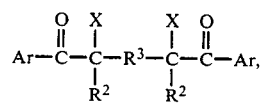

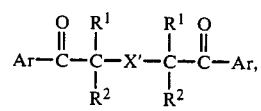

in which Ar is a sulfur-containing aromatic radical, selected from one of the following formulae

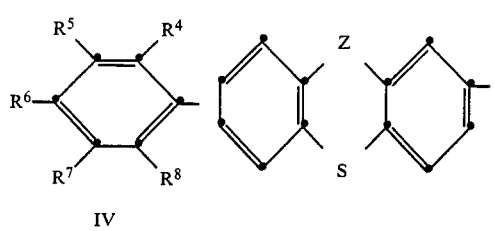

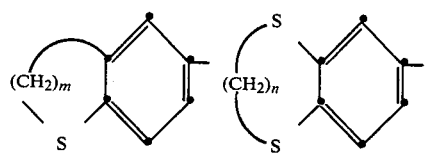

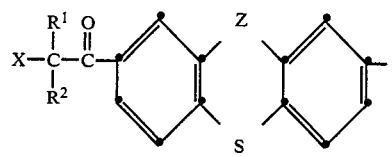

in which m is 2 or 3 and n is 1, 2 or 3, Z is a direct bond, $-CH_2-$, $-CH_2CH_2-$, $-O-$ or $-S-$, $R^4$, $R^5$, $R^6$, $R^7$ and $R^8$ independently of one another are hydrogen, halogen, $C_1$-$C_4$-alkyl, $C_3$-$C_{12}$-alkenyl, $C_5$-$C_6$-cycloalkyl, phenyl, $C_1$-$C_4$-alkoxy, $C_1$-$C_4$-hydroxyalkoxy, phenoxy, $-COOH$, $-COO(C_1$-$C_4$-alkyl), $-S-R^9$, $-SO-R^9$ or $-SO_2R^9$, but at least one of the radicals $R^4$ to $R^8$ is a group $-S-R^9$ or $-SO-R^9$, $R^9$ is hydrogen, $C_1$-$C_{12}$-alkyl, $C_3$-$C_{12}$-alkenyl, cyclohexyl, hydroxycyclohexyl, $C_1$-$C_4$-alkyl which is substituted by Cl, CN, SH, $-N(C_1$-$C_4$-alkyl$)_2$, piperidino, morpholino, OH, $-O(C_1$-$C_4$-alkyl), $-OCH_2CH_2CN$, $-OCH_2CH_2COO-(C_1$-$C_4$-alkyl), $-OOC-R^{10}$, $-COOH$, $-COO-(C_1$-$C_8$-alkyl), $-CON-(C_1$-$C_4$-alkyl$)_2$,

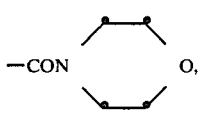

—CO—($C_1$-$C_4$-alkyl) or —CO—phenyl, 2,3-dihydroxypropyl, 2,3-epoxypropyl, phenyl, $C_7$-$C_9$-phenylalkyl, $C_7$-$C_9$-phenylhydroxyalkyl, phenyl which is substituted by halogen, $C_1$-$C_4$-alkyl, $C_1$-$C_4$-alkoxy or —COO—($C_1$-$C_4$-alkyl), 2-benzthiazolyl, 2-benzimidazolyl or a radical of the formulae

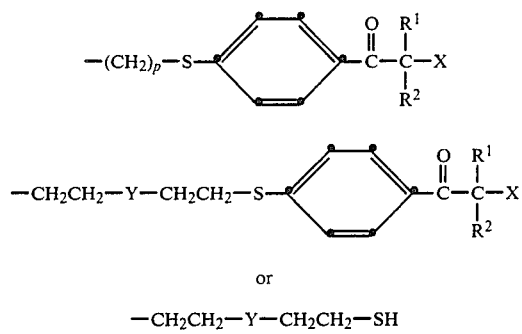

or

—$CH_2CH_2$—Y—$CH_2CH_2$—SH in which p is 0 to 4 and Y is oxygen or sulfur, or $R^9$ is a radical of the formula

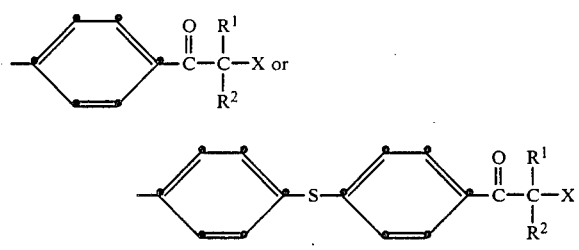

$R^{10}$ is $C_1$-$C_4$-alkyl, $C_2$-$C_4$-alkenyl or phenyl, X is an amino group —$N(R^{11})(R^{12})$, X′ is a divalent radical of the formula

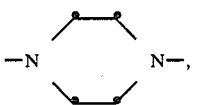

—$N(R^{13})$— or —$N(R^{13})$—$(CH_2)_x$—$N(R^{13})$— in which x is 1 to 8, $R^{11}$ is hydrogen, $C_1$-$C_{12}$-alkyl, $C_2$-$C_4$-alkyl which is substituted by OH, $C_1$-$C_4$-alkoxy or CN, $C_3$-$C_5$-alkenyl, cyclohexyl, $C_7$-$C_9$-phenylalkyl, phenyl or phenyl which is substituted by Cl, $C_1$-$C_4$-alkyl, $C_1$-$C_4$-alkoxy or —COO—($C_1$-$C_4$-alkyl), or $R^{11}$ and $R^1$ together are the group —$CH_2OCH_2$—, $R^{12}$ has one of the meanings given for $R^{11}$ or, together with $R^{11}$, is $C_3$-$C_7$-alkylene which can be interrupted by —O—, —S— or —$N(R^{14})$—, or $R^{12}$, together with $R^2$, is $C_1$-$C_8$-alkylene, $C_7$-$C_{10}$-phenylalkylene, o-xylylene or $C_1$-$C_3$-oxaalkylene or $C_1$-$C_3$-azaalkylene, $R^{13}$ is hydrogen, $C_1$-$C_9$-alkyl, $C_1$-$C_4$-hydroxyalkyl, cyclohexyl or benzyl, $R^{14}$ is hydrogen, $C_1$-$C_4$-alkyl, $C_1$-$C_4$-hydroxyalkyl, —$CH_2CH_2CN$ or —$CH_2CH_2COO$—($C_1$-$C_4$-alkyl), $R^1$ and $R^2$ independently of one another are $C_1$-$C_8$-alkyl, $C_1$-$C_4$-alkyl which is substituted by OH, $C_1$-$C_4$-alkoxy, CN, —COO—($C_1$-$C_8$-alkyl) or —$N(R^{11})(R^{12})$, phenyl, chlorophenyl, $R^9$—S—phenyl or $C_7$-$C_9$-phenylalkyl, or $R^1$ and $R^2$ together are $C_2$-$C_8$-alkylene, $C_3$-$C_9$-oxaalkylene or $C_3$-$C_9$-azaalkylene, and $R^3$ is a direct bond, $C_1$-$C_6$-alkylene, $C_2$-$C_6$-oxaalkylene or cyclohexylene or, together with the two substituents $R^2$ and the two C atoms to which these substituents are attached, forms a cyclopentane, cyclohexane, cyclohexene, endomethylenecyclohexane or endomethylenecyclohexene ring.

In the above, $R^9$ as alkyl can be linear or branched alkyl, or example methyl, ethyl, isopropyl, n-butyl, iso-butyl, tert.-butyl, isoamyl, n-hexyl, n-octyl, 2-ethylhexyl, n-decyl or n-dodecyl.

As alkenyl, $R^9$ can be, for example, allyl, methallyl or undecenyl.

As substituted alkyl $R^9$ can be, for example, 2-chloroethyl, 2-chloropropyl, cyanomethyl, 2-cyanoethyl, 2-mercaptoethyl, dimethylaminomethyl, morpholinomethyl, 2-piperidinoethyl, 2-morpholinoethyl, 2-hydroxyethyl, 2-hydroxypropyl, 2-butoxyethyl, 2-ethoxybutyl, 2-methoxymethyl, 2-(2′-cyanoethoxy)-propyl, 2-(2′-ethoxycarbonylethoxy)ethyl, 2-acetoxyethyl, 2-acryloyloxypropyl, 2-benzoyloxymethyl, carboxymethyl, 2-methoxycarbonylethyl, butoxycarbonylmethyl, n-octyloxycarbonylmethyl, 2-diethylcarbamoylethyl, morpholinocarbonylmethyl, 2-isobutyroylethyl, 2-benzoylethyl or acetylmethyl.

A phenylalkyl or phenylhydroxyalkyl radical $R^9$ can be, for example, benzyl, phenylethyl, phenylpropyl, phenylhydroxymethyl or 2-phenyl-2-hydroxyethyl.

As substituted phenyl, $R^9$ can be, for example, 4-chlorophenyl, 3-bromophenyl, 2-fluorophenyl, p-tolyl, p-isopropylphenyl, 2,4-dimethylphenyl, 4-methoxyphenyl, 3-ethoxy-p-tolyl, 3-methoxycarbonylphenyl or 4-butoxycarbonylphenyl.

X can be a primary, secondary or tertiary amino group; preferably, X is a tertiary amino group. The substituents $R^{11}$ and $R^{12}$ can be aliphatic, cycloaliphatic, aromatic or araliphatic groups. Examples of $R^{11}$ and $R^{12}$ are the groups methyl, ethyl, propyl, butyl, hexyl, octyl, 2-ethylhexyl, dodecyl, 2-hydroxyethyl, 2-hydroxybutyl, 2-methoxypropyl, 2-ethoxyethyl, 2-cyanoethyl, allyl, methallyl, cyclohexyl, benzyl, phenylethyl, phenyl, 4-chlorophenyl, 4-tolyl, 3-hydroxyphenyl, 3-methoxyphenyl, 4-ethoxyphenyl, 4-methoxycarbonylphenyl or 2,4-dimethylphenyl. If $R^{11}$ and $R^{12}$ together are alkylene or interrupted alkylene, X can be, for example, a pyrrolidino, oxazolidino, piperidino, 3,5-dimethylpiperidino, morpholino, thiomorpholino, piperazino, 4-methylpiperazino, 4-(cyanoethyl)-piperazino or 4-(hydroxyethyl)-piperazino group. If $R^{12}$ together with $R^2$ forms an alkylene, phenylalkylene, o-xylylene, oxaalkylene or azaalkylene radical, these radicals can, together with the C atom to which $R^2$ and $R^{12}$ are attached, form, for example, an aziridine, pyrrolidine, piperidine, tetrahydroisoquinoline, phenylaziridine, methylpyrrolidine, dimethylpiperidine or morpholine ring. If $R^{11}$ and $R^1$ together are —$CH_2OCH_2$—, these radicals, together with the nitrogen atom and the quaternary carbon atom, form an oxazolidine ring. If $R^{12}$ and $R^2$ also form an oxazolidine ring of this type, this results in compounds of the formula

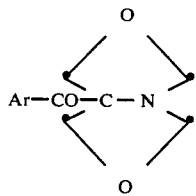

X is preferably a morpholino radical or a radical of the formula —N—(CH$_2$CH$_2$OCH$_3$)$_2$. X' is a divalent, secondary or tertiary amino or diamino group. Examples of diamino groups —N(R$^{13}$)—(CH$_2$)$_x$—N(R$^{13}$)— are, in particular, groups in which x=1, 2, 3, 4 and 6.

As alkyl or substituted alkyl, R$^1$ and R$^2$ can be, for example, methyl, ethyl, propyl, butyl, isopentyl, hexyl, isooctyl, hydroxymethyl, methoxymethyl, 2-cyanoethyl, 2-methoxycarbonylethyl, 2-butoxycarbonylethyl, dimethylaminomethyl or 3-aminopropyl. If R$^1$ and R$^2$ together are alkylene, oxaalkylene or azaalkylene, they form, together with the C atom to which they are attached, for example, a cyclopentane, cyclohexane, cyclooctane, tetrahydropyran, pyrrolidine or piperidine ring. R$^1$ and R$^2$ are preferably C$_1$-C$_4$-alkyl, in particular methyl, or R$^1$ and R$^2$ together are C$_2$-C$_8$-alkylene, in particular pentamethylene.

As alkylene, R$^3$ can be a linear or branched alkylene radical, for example methylene, ethylene, trimethylene, tetramethylene, pentamethylene, hexamethylene, 2,2-dimethyl-1,3-propylene or 2,3-dimethyl-1,4-butylene. As oxaalkylene, R$^3$ can be, for example, 2-oxa-1,3-propylene or 3-oxa-1,5-pentylene.

Compounds of the formula I, II or III which are preferred as photoinitiators are those in which Ar is a radical of the formula IV in which at least one of the radicals R$^4$ to R$^8$ is a group —S—R$^9$. This group is preferably in the 4-position. The other positions of the phenyl radical can either be unsubstituted or can also be a group —S—R$^9$ or can be another of the substituents R$^4$ to R$^8$ defined above, in particular an alkoxy radical. In this case R$^9$ is as defined above.

Preferred photoinitiators are, furthermore, compounds of the formula I, in particular compounds of the formula I in which Ar is a phenyl radical which is substituted by 1 or 2 of the groups —S—R$^9$ and can be substituted by 1 or 2 alkoxy groups, R$^9$ is hydrogen, C$_1$-C$_{12}$-alkyl, C$_3$-C$_6$-alkenyl, cyclohexyl, C$_7$-C$_9$-phenylalkyl, phenyl, phenyl which is substituted by C$_1$-C$_4$-alkyl, or one of the groups —CH$_2$—CH$_2$OH, —CH$_2$CH$_2$—OOC—CH=CH$_2$, —CH$_2$CN, —CH$_2$COOH, —CH$_2$COO(C$_1$-C$_8$-alkyl), —CH$_2$CH$_2$CN, —CH$_2$CH$_2$COO(C$_1$-C$_8$-alkyl),

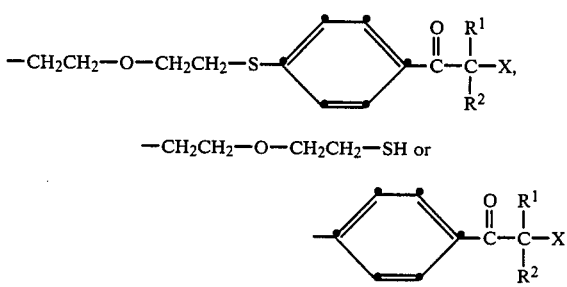

or R$^1$ and R$^2$ independently of one another are C$_1$-C$_4$-alkyl, phenyl or C$_7$-C$_9$-phenylalkyl, or R$^1$ and R$^2$ together are C$_2$-C$_8$-alkylene and X is an amino group —N(R$^{11}$)(R$^{12}$) in which R$^{11}$ is C$_1$-C$_8$-alkyl, C$_2$-C$_4$-alkyl which is substituted, by OH, C$_1$-C$_4$-alkoxy or CN, or C$_3$-C$_5$-alkenyl and R$^{12}$ has one of the meanings given for R$^{11}$ or, together with R$^{11}$, is C$_4$-C$_5$-alkylene which can be interrupted by —O—, —S— or —N(R$^{14}$)—, R$^{14}$ being C$_1$-C$_4$-alkyl, 2-cyanoethyl, 2-hydroxyethyl or 2-hydroxypropyl.

Compounds of the formula I which are particularly preferred as photoinitiators are those in which Ar is a phenyl radical which is substituted by the group —S—R$^9$ and R$^9$ is hydrogen, C$_1$-C$_8$-alkyl, C$_3$-C$_6$-alkenyl, cyclohexyl, benzyl, phenyl, tolyl or one of the groups —CH$_2$—CH$_2$OH, —CH$_2$CH$_2$—OOC—CH=CH$_2$, —CH$_2$—COO(C$_1$-C$_4$-alkyl), —CH$_2$CH$_2$—COO(C$_1$-C$_4$-alkyl),

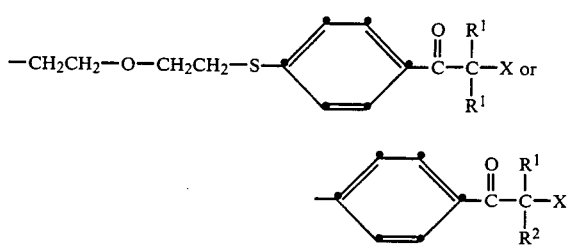

R$^1$ and R$^2$ are C$_1$-C$_4$-alkyl, or R$^1$ and R$^2$ together are C$_4$-C$_5$-alkylene and X is a morpholino radical or a radical of the formula —N—(CH$_2$CH$_2$OCH$_3$)$_2$.

Photoinitiators of the formula I which are particularly preferred are, in particular, those in which Ar is 4-mercaptophenyl, 4-methylthiophenyl or 4-(2-hydroxyethyl)thiophenyl, R$^1$ and R$^2$ independently of one another are methyl, ethyl or butyl and X is a morpholino group.

The following compounds are examples of individual compounds of the formula I: 2-methyl-1-[4-(methylthio)phenyl]-2-morpholinopropan-1-one, 2-methyl-1-[4-(ethylthio)phenyl]-2-morpholinopropan-1-one, 2-methyl-1-[4-(butylthio)phenyl]-2-morpholinopropan-1-one, 2-methyl-1-[4-(octylthio)phenyl]-2-morpholinopropan-1-one, 2-methyl-1-[4-(dodecylthio)-phenyl]-2-morpholinopropan-1-one, 2-methyl-1-[4-(mercaptophenyl]-2-morpholinopropan-1-one, 2-methyl-1-[4-(2-hydroxyethylthio)-phenyl]-2-morpholinopropan-1-one, 2-methyl-1-[4-(2-acetoxyethylthio)phenyl]-2-morpholinopropan-1-one, 2-methyl-1-[4-(2-acryloyloxyethylthio)-phenyl]-2-morpholinopropan-1-one, 2-methyl-1-[4-(2,3-dihydroxypropylthio)-phenyl]-2-morpholinopropan-1-one, 2-methyl-1-[4-(2,3-epoxypropylthio)-phenyl]-2-morpholinopropan-1-one, 2-methyl-1-[4-(2-(2-mercaptoethoxy)-ethylthio)-phenyl]-2-morpholinopropan-1-one, 2-methyl-1-[4-(phenylthio)-phenyl]-2-morpholinopropan-1-one, 2-methyl-1-[4-(2-benzothiazolthio)phenyl]-2-morpholinopropan-1-one, 2-methyl-1-[4-(2-benzimidazolthio)-phenyl]-2-morpholinopropan-1-one, 2-methyl-1-[4-(octyloxycarbonylmethylthio)-phenyl]-2-morpholinopropan-1-one, 2-methyl-1-[4-(methoxycarbonylmethylthio)phenyl]-2-morpholinopropan-1-one, 2-methyl-1-[4-(2-ethylhexyloxycarbonylmethylthio)-phenyl]-2-piperidinopropan-1-one, 2-methyl-1-[4-(phenylthio)-phenyl]-2-piperidinopropan-1-one, 2-methyl-1-[4-(methylthio)-phenyl]-2-pyrrolidinopropan-1-one, 2-methyl-1-[4-(methylthio)-phenyl]-2-oxazolidinopropan-1-one, 2-methyl-1-[4-(methylthio)-phenyl]-2-(4-methylpiperazino)-propan-1-one, 2-methyl-1-[4-(phenylthio)-phenyl]-2-(4-methylpiperazino)-propan-1-one, 2-methyl-1-[4-(methylthio)-phenyl]-2-dibutylaminopropan-1-one, 2-methyl-1-[4-(methylthio)-phenyl]-2-diethylaminopropan-1-one, 2-methyl-1-[4-methylthio)-phenyl]-2-dimethylaminopropan-1-one, 2-methyl-1-[4-(methylthio)-phenyl]-2-methylphenylaminopropan-1-one, 2-methyl-1-[4-(methylthio)-phenyl]-2-butylaminopropan-1-one, 2-methyl-1-[4-(methylthio)-phenyl]-2-di-(2-ethylhexyl)-aminopropan-1-one, 2-methyl-1-[4-(methylthio)-phenyl]-2-di-(2-methoxyethyl)-aminopropan-1-one, 2-methyl-1-[4-(phenylthio)-phenyl]-2-di-(2-methoxyethyl)-aminopropan-1-one, 2-methyl-1-[4-(phenylthio)-phenyl]-2-dibutylaminopropan-1-one, 2-methyl-1-[4-(methylthio)-phenyl]-2-methyl-1-[4-(2-hydroxyethoxy)-3-(2-hydroxyethylthio)-phenyl]-2-morpholino-propanon-1, 2-methyl-1-[4-methylthio)-phenyl]-2-piperazinopropan-1-one, 4,4'-bis-(α-morpholinoisobutyroyl)-diphenyl sulfide, 2,2'-bis-[4-(α-morpholinoisobutyroyl)-phenylthio]-diethyl ether, 2-ethyl-1-[4-(methylthio)-phenyl]-2-morpholinohexan-1-one, 1-(4-methylthiobenzoyl)-1-piperidinocyclohexane, 1-(4-methylthiobenzoyl)-1-morpholinocyclohexane, 2-methyl-1-[4-(ethylthio)-phenyl]-2-aminopropan-1-one, 2-methyl-1-[4-(methylthio)-phenyl]-2-aminopropan-1-one, 2-methyl-1-[4-(ethylthio)-phenyl]-2-methylaminopropan-1-one, 1-(4-ethylthiobenzoyl)-1-methylaminocyclohexane, 2-methyl-1-[4-(methylthio)-phenyl]-2-morpholinobutan-1-one, 2-methyl-1-[4-(methylthio)-phenyl]-2-morpholinopentan-1-one, 2-ethyl-1-[4-(methylthio)-phenyl]-2-morpholinobutan-1-one, 2-propyl-1-[4-(methylthio)-phenyl]-2-morpholinopentan-1-one, 2-methyl-1-[4-(cyanomethylthio)-phenyl]-2-morpholinopropan-1-one, 2-methyl-1-[4-(2-cyanoethylthio)-phenyl]-2-morpholinopropan-1-one, 2-methyl-1-[4-(2-ethoxycarbonylethylthio)-phenyl]-2-morpholinopropan-1-one, 2-methyl-1-[4-(benzylthio)-phenyl]-2-morpholinopropan-1-one, 2-methyl-1-[4-(cyclohexylthio)-phenyl]-2-morpholinopropan-1-one, 2-methyl-1-[4-(carboxymethylthio)-phenyl]-2-morpholinopropan-1-one, 2-methyl-1-[4-(ethoxycarbonylmethylthio)-phenyl]-2-morpholinopropan-1-one, 2-methyl-1-[3-(methylthio)-phenyl]-2-morpholinopropan-1-one, 2-methyl-1-[2-(methylthio)-phenyl]-2-morpholinopropan-1-one, 2-methyl-1-[3,4-bis-(methylthio)-phenyl]-2-morpholinopropan-1-one, 2-methyl-1-[4-(methylsulfinyl)-phenyl]-2-morpholinopropan-1-one, 2-methyl-1-[4-(phenylsulfinyl)-phenyl]-2-morpholinopropan-1-one, 2-ethyl-1-[4-(isopropylthio)-phenyl]-2-morpholinobutan-1-one, 2-methyl-1-[4-(allylthio)-phenyl]-2-morpholinopropan-1-one, 2-methyl-1-[4-(methallylthio)-phenyl]-2-morpholinopropan-1-one, 2-methyl-1-[4-(2-chloroethylthio)-phenyl]-2-pyrrolidinopropan-1-one, 2-methyl-1-[4-(3-bromo-4-methoxyphenylthio)-phenyl]-2-morpholinopropan-1-one, 2-methyl-1-[3-(2-chloro-4-isopropylphenylthio)-phenyl]-2-morpholinopropan-1-one, 2-methyl-1-[4-(3,4-bis-ethoxycarbonylphenylthio)-phenyl]-2-morpholinopropan-1-one, 2-methyl-1-[4-(2-methacryloyloxyethylthio)-phenyl]-2-morpholinopropan-1-one, 2-ethyl-1-[4-(2-(2-cyanoethoxy)-ethylthio)-phenyl]-2-morpholinohexan-1-one, 4,4'-bis-(α-morpholinoisobutyroyl)-diphenyl disulfide, 1,2-bis-[4-(α-morpholinoisobutyroyl)phenylthio]-ethane, bis-[4-(α-morpholinoisobutyroyl)-phenylthio]-methane, 2,2'-bis-[4-(α-morpholinoisobutyroyl)-phenylthio]-diethyl sulfide, 2-methyl-1-[4-(2-butyroyloxyethylthio)-phenyl]-2-morpholinopropan-1-one, 1,4-bis-[4-(α-morpholinoisobutyroyl)-phenylthio]-benzene, 2-methyl-1-[4-(2-butyloxycarbonylpropyl)-thiophenyl]-2-morpholinopropan-1-one, 2-methyl-1-[4-(2-benzoyloxyethyl)-thiophenyl]-2-morpholinopropan-1-one, 2-methyl-1-[4-(2-carboxyethyl)-thiophenyl]-2-morpholinopropan-1-one, 2-methyl-1-[4-(dimethylaminocarbonylmethylthio)-phenyl]-2-dimethylaminopropan-1-one, 2-methyl-1-[4-(dibutylaminocarbonylmethylthio)phenyl]-2-dibutylaminopropan-1-one, 2-methyl-1-[4-(morpholinocarbonylmethylthio)-phenyl]-2-morpholinopropan-1-one, 2-methyl-1-[4-(morpholinocarbonylethylthio)-phenyl]-2-morpholinopropan-1-one, 2-methyl-1-[4-(2-diethylaminocarbonylethylthio)-phenyl]-2-dimethylaminopropan-1-one, 2-methyl-1-[4-(2-ethoxyethylthio)-phenyl]-2-morpholinopropan-1-one, 2-methyl-1-[4-(3-oxobutylthio)-phenyl]-2-morpholinopropan-1-one, 2-ethyl-1-[4-(3-phenyl-3-oxopropylthio)-phenyl]-2-morpholinohexan-1-one, 2-methyl-1-[4-(methylthio)-3-methylphenyl]-2-morpholinopropan-1-one, 1-[4-chloro-3-(methylthio)-benzoyl]-1-morpholinocyclohexane, 2-methyl-1-[4-(ethylthio)-2-(methoxycarbonyl)phenyl]-2-morpholinopropan-1-one, 2-methyl-1-[4-(2-hydroxyethylthio)-3-methoxyphenyl]-2-morpholinopropan-1-one, 2-methyl-1-[3-chloro-4-(3-mercaptopropylthio)-phenyl]-2-morpholinopropan-1-one, 2-methyl-1-[2,3,4,5,6-pentakis-(methylthio)-phenyl]-2-morpholinopropan-1-one, 2-methyl-1-[3,4-bis-(2-hydroxyethylthio)-5-chlorophenyl]-2-morpholinopropan-1-one, 2-methyl-1-(2-thianthrenyl)-2-dimethylaminopropan-1-one, 2-methyl-1-(2-thianthrenyl)-2-morpholinopropan-1-one, 2-methyl-1-(3-phenoxyanthinyl)-2-morpholinopropan-1-one, 2-methyl-1-(3-phenoxyanthinyl)-2-dibutylaminopropan-1-one, 2-methyl-1-(3-thioxanthenyl)-2-morpholinopropan-1-one, 1-(3,4-dihydro-2H-1-benzothiopyran-6-yl)-2-methyl-2-morpholinopropan-1-one, 1-(2,3-dihydrobenzo[b]thiophen-5-yl)-2-methyl-2-di-(2-methoxyethyl)-aminopropan-1-one, 1-(1,3-benzodithiol-5-yl)-2-ethyl-2-morpholinopropan-1-one, 1-(2,3-dihydro-1,4-benzotithiin-6-yl)-2-methyl-2-pyrrolidinopropan-1-one, 1-(3,4-dihydro-2H-1,5-benzodithiepin-7-yl)-2-methyl-2-morpholinopropan-1-one, 2,7-bis-(α-morpholinoisobutyroyl)-thioxanthene, 3,7-bis-(α-morpholinoisobutyroyl)-phenoxathiin, 2,8-bis-(α-morpholinoisobutyroyl)-thianthrene, 2-methyl-1-[4-(ethylthio)-phenyl]-2-morpholinobutan-1-one, 1-[4-(methylthio)-phenyl]-2-morpholino-2-phenylpropan-1-one, 1-[4-(isopropylthio)-phenyl]-2-piperidino-2-phenylpropan-1-one, 2,2-diphenyl-1-[4-(methylthio)-phenyl]-2-morpholinoethan-1-one, 1,2-bis-[4-(methylthio)phenyl]-2-morpholinopropan-1-one, 2-methyl-1-[4-(methylthio)-phenyl]-2,3-dimorpholino-3-phenylpropan-1-one, 2-methyl-1-[4-(methylthio)-phenyl]-2,3-dimorpholinopropan-1-one, 2-methyl-3-methoxy-1-[4-(methylthio)-phenyl]-2-morpholinopropan-1-one, 3-ethoxy-2-methyl-1-[4-(2-hydroxyethylthio)-phenyl]-2-morpholinopropan-1-one, 4-ethoxycarbonyl-2-methyl-1-[4-(ethylthio)-phenyl]-2-morpholinobutan-1-one, 1-(dibenzothien-2-yl)-2-ethyl-2-morpholinobutan-1-one, 1-[4-(methylthio)-phenyl]-2-methyl-2-morpholino-4-cyanobutan-1-one, 2-methyl-1-[4-(2-hydroxyethylthio)-phenyl]-2-morpholino-5-(di-2-hydroxyethylamino)-pentan-1-one, 2-methyl-1-[4-(methylthio)-phenyl]-2-morpholino-3-phenylpropan-1-one, 2-morpholino-1-[4-(methylsulfinyl)-phenyl]-2-benzyl-3-phenylpropan-1-one, 1-(4-methylthiobenzoyl)-1-dimethylaminocyclohexane, 1,2-dimethyl-2-(4-methylthiobenzoyl)-piperidine, 1-(4-methylthiobenzoyl)-1-morpholinocyclopentane, 1-(3-methylthiobenzoyl)-1-morpholinocyclopropane, 1-(4-tert.-butylthiobenzoyl)-1-morpholinocyclohex-3-ene, 3-(4-methylthiobenzoyl)-3-morpholinotetrahydropyran, 3,4-dimethyl-4-(4-dodecylthiobenzoyl)-oxazolidine, 2-methyl-1-[4-(methylthio)-phenyl]-2-dodecylaminopropan-1-one, 2-ethyl-1-[4-(methylthio)-phenyl]-2-ethylaminohexan-1-one, 2-methyl-1-[4-(methylthio)-phenyl]-2-di-(2-cyanoethyl)-aminopropan-1-one, 2-methyl-1-[4-(allylthio)-phenyl]-2-diallylaminopropan-1-one, 2-methyl-1-[4-(ethylthio)-phenyl]-2-di-(2-hydroxyethyl)-aminopropan-1-one, 2-methyl-1-[4-(butylthio)-phenyl]-2-(hexylmethylamino)-propan-1-one, 2-methyl-1-[4-(benzylthio)-phenyl]-2-dibenzylaminopropan-1-one, 2-methyl-1-[4-(methylthio)-phenyl]-2-(N-ethylphenylamino)-propan-1-one, 2-methyl-1-[4-(methylthio)-phenyl]-2-(N-methyl-4-ethoxycarbonylphenylamino)-propan-1-one, 2-methyl-1-[4-(methylthio)-phenyl]-2-(4-methoxy-3-methylphenylamino)-propan-1-one, 2-methyl-1-[4-(methylthio)-phenyl]-2-(N-methyl-4-chloro-3-ethoxyphenylamino)-propan-1-one, 3,4-dimethyl-4-(4-methylthiobenzoyl)-oxazolidine, 7α(7H)-(4-methylthiobenzoyl)-1H,3H,5H-oxazolo-[3,4-c]oxazole, 2-methyl-1-[4-(methylthio)-phenyl]-2-thiomorpholinopropan-1-one, 2-methyl-1-[4-(methylthio)-phenyl]-2-oxazolidinopropan-1-one, 2-methyl-1-[4-(methylthio)phenyl]-B 2-[4-(2-hydroxyethyl)]-piperazinopropan-1-one, 2-methyl-1-[4-(methylthio)-phenyl]-2-[4-(2-cyanoethyl)]-piperazinopropan-1-one, 2-methyl-1-[4-(methylthio)-phenyl]-2-[4-(2-ethoxycarbonylethyl)]-piperazinopropan-1-one, 2-methyl-2-(4-methylthiobenzoyl)-pyrrolidine 1-(2-hydroxyethyl)-2-methyl-2-[4-(2-hydroxyethylthio)-benzoyl]-pyrrolidine, 2-methyl-1-[3-(methylsulfinyl)-4-(methylthio)-phenyl]-2-morpholinopropan-1-one, 2-methyl-1-[3-(methylsulfo)-4-(methylthio)-phenyl]-2-morpholinopropan-1-one, 2-methyl-1-[3-(methylsulfo)-4-(methylsulfinyl)-phenyl]-2-morpholinopropan-1-one, 2-methyl-1-[3-(phenylsulfo)-4-(phenylthio)-phenyl]-2-morpholinopropan-1-one, 2-methyl-1-[4-(dimethylaminomethylthio)-phenyl]-2-morpholinopropan-1-one, 2-methyl-1-[4-(diethylaminomethylthio)-phenyl]-2-morpholinopropan-1-onw, 2-methyl-1-[4-(2-methoxycarbonylethylthio)-phenyl]-2-morpholinopropan-1-one, 2-methyl-1-[4-(acetylthio)phenyl]-2-morpholinopropan-1-one, 2-methyl-1-[4-(4-tolylthio)-phenyl]-2-morpholinopropan-1-one, 2-methyl-1-[4-(2-(ethoxycarbonyl)-phenylthio)-phenyl]-2-morpholinopropan-1-one, 3-[4-(ethylthio)-benzoyl]-3-methyl-1,2,3,4-tetrahydroisoquinoline, 2-methyl-1-[3,4,5-tris-(methylthio)-phenyl]-2-morpholinopropan-1-one, 2-methyl-1-[3,4,5-tris-(2-hydroxyethylthio)-phenyl]-2-morpholinopropan-1-one, 2-methyl-1-[4-(methylthio)-3-phenoxyphenyl]-2-morpholinopropan-1-one, 2-methyl-1-[4-(methylthio)-3-methoxyphenyl]-2-morpholinopropan-1-one, 2-methyl-1-[3-(methylthio)-4-methoxyphenyl]-2-morpholinopropan-1-one, 2-methyl-1-[4-(methylthio)-3-chlorophenyl]-2-morpholinopropan-1-one, 2-methyl-1-[5-(methylthio)-2-methoxyphenyl]-2-morpholinopropan-1-one, 2-methyl-1-[3,5-bis-(methylthio)-2-methoxyphenyl]-2-morpholinopropan-1-one, 2-methyl-1-[3-(methylthio)-4,5-dimethoxyphenyl]-2-morpholinopropan-1-one, 2-methyl-1-[4-(methylthio)-5-bromo-2-methoxyphenyl]-2-morpholinopropan-1-one, 2-methyl-1-[5-(methylthio)-2-bromo-4-methoxyphenyl]-2-morpholinopropan-1-one, 2-methyl-1-[4-(methylthio)-3,5-dichlorophenyl]-2-morpholinopropan-1-one, 2-methyl-1-[4-(methylthio)-2,3,5-trimethylphenyl]-2-morpholinopropan-1-one, 2-methyl-1-[4-(butylthio)-3-butoxyphenyl]-2-morpholinopropan-1-one, 2-methyl-1-[4-(ethylthio)-3-chloro-5-methylphenyl]-2-morpholinopropan-1-one, 2-methyl-1-[3-(methylthio)-4-ethoxy-5-methylphenyl]-2-morpholinopropan-1-one, 2-methyl-1-[4-(2-hydroxyethylthio)-2-chloro-5-methoxyphenyl]-2-morpholinopropan-1-one, 2-methyl-1-[4-(2-hydroxycyclohexylthio)-phenyl]-2-morpholinopropan-1-one, 2-methyl-1-[4-(morpholinomethylthio)-phenyl]-2-morpholinopropan-1-one.

The following compounds are examples of compounds of the formula II: 1,4-bis-[4-(methylthio)-phenyl]-2,3-dimethyl-2,3-dimorpholino-1,4-butanedione, 1,5-bis-[4-(2-hydroxyethylthio)-phenyl]-2,4-dimethyl-2,4-dimorpholino-1,5-pentanedione, 1,10-bis-[4-(isopropylthio)-phenyl]-2,9-dimethyl-2,9-dimorpholino-1,10-decanedione, 1,2-bis-[4-(methylthio)-benzoyl]-1,2-bis-(dimethylamino)-cyclohex-4-ene, 1,4-bis-[4-(methylthio)-benzoyl]-1,4-dimorpholinocyclohexane, 1,7-bis-[4-(methylthio)-phenyl]-2,6-dimethyl-2,6-dimorpholino-4-oxa-1,7-heptanedione,α,α′-bis[4-(methylthio)-benzoyl]-α,α′-dimorpholino-1,4-diethylcyclohexane, 1,3-bis-[4-(methylthio)-benzoyl]-1,3-bis-(diethylamino)-cyclopentane, 2,3-bis-(4-methylthiobenzoyl)-2,3-dipiperidinobicyclo[2.2.1]heptane, 2,3-bis-(4-ethylthiobenzoyl)-2,3-dimorpholinobicyclo[2.2.1]hept-5-ene.

The following compounds are examples of compounds of the formula III: N,N′-bis-[α-(4-methylthiobenzoyl)-isopropyl]-piperazine, N,N-bis-[α-(4-mercaptobenzoyl)-isopropyl]-benzylamine, N,N′-bis-[α-(4-ethylthiobenzoyl)-isopropyl]-hexamethylenediamine, N,N′-dimethyl-N,N′-bis-[α-(4-methylthiobenzoyl)-isopropyl]-hexamethylenediamine.

Some of the compounds of the formula I, II and III are known compounds, the general preparation of which is described in European Patent Application Publication No. 3002. Others are novel compounds which also form the subject of the present invention. These are compounds of the formula I, II and II in which Ar is a sulfur-containing aromatic radical, selected from one of the following formulae:

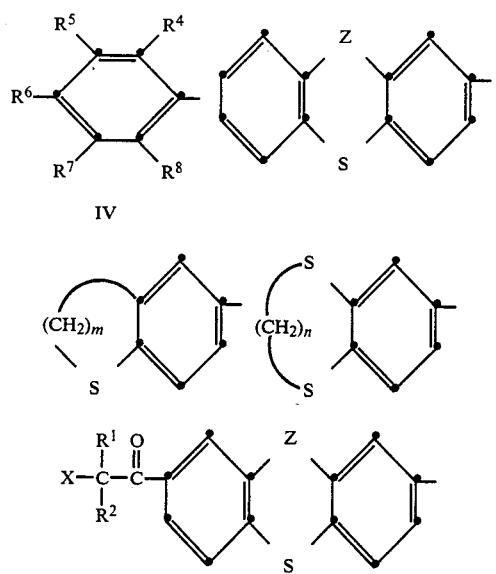

in which m is 2 or 3 and n is 1, 2 or 3, Z is a direct bond, —CH$_2$—, —CH$_2$CH$_2$—, —O— or —S—, $R^4$, $R^5$, $R^6$, $R^7$ and $R^8$ independently of one another are hydrogen, halogen, $C_1$-$C_4$-alkyl, $C_3$-$C_{12}$-alkenyl, $C_5$-$C_6$-cycloalkyl, phenyl, $C_1$-$C_4$-alkoxy, $C_1$-$C_4$-hydroxyalkoxy, phenoxy, —COOH, —COO—($C_1$-$C_4$-alkyl), —S—$R^9$, —SO—$R^9$ or —$SO_2$—$R^9$, but at least one of the radicals $R^4$ to $R^8$ is a group —S—$R^9$ or —SO—$R^9$, $R^9$ is hydrogen, $C_5$-$C_{12}$-alkyl, $C_3$-$C_{12}$-alkenyl, cyclohexyl, hydroxycyclohexyl, $C_1$-$C_4$-alkyl which is substituted by Cl, CN, SH, —N—($C_1$-$C_4$-alkyl)$_2$, piperidino, morpholino, —O—($C_1$-$C_4$-alkyl), —$OCH_2CH_2CN$, —$OCH_2CH_2COO$—($C_1$-$C_4$-alkyl), —OOC—$R^{10}$, —COOH, —COO—($C_1$-$C_8$-alkyl), —CON—($C_1$-$C_4$-alkyl)$_2$,

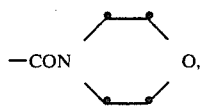

—CO—($C_1$-$C_4$-alkyl) or —CO—phenyl, 2-hydroxypropyl, 2,3-dihydroxypropyl, 2,3-epoxypropyl, $C_7$-$C_9$-phenylalkyl, $C_7$-$C_9$-phenylhydroxyalkyl, phenyl which is substituted by halogen, $C_1$-$C_4$-alkyl, $C_1$-$C_4$-alkoxy or —COO—($C_1$-$C_4$-alkyl), 2-benzthiazolyl, 2-benzimidazolyl or a radical of the formulae

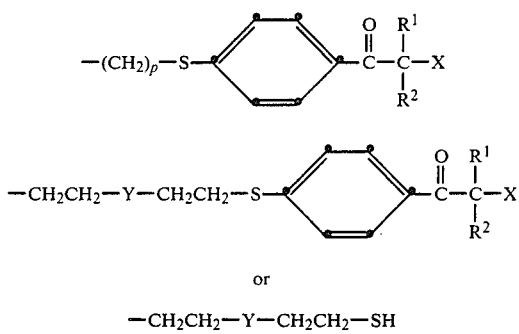

or

—$CH_2CH_2$—Y—$CH_2CH_2$—SH in which p is zero to 4 and Y is oxygen or sulfur, or $R^9$ is a radical of the formula

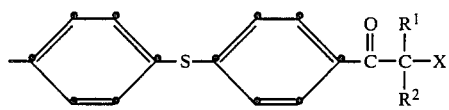

$R^{10}$ is $C_1$-$C_4$-alkyl, $C_2$-$C_4$-alkenyl or phenyl, X is an amino group —N($R^{11}$)($R^{12}$), X' is a divalent radical of the formula

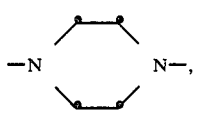

—N($R^{13}$)— or —N—($R^{13}$)—($CH_2$)$_x$—N($R^{13}$)— in which x is 1 to 8, $R^{11}$ is hydrogen, $C_1$-$C_{12}$-alkyl, $C_2$-$C_4$-alkyl which is substituted by OH, $C_1$-$C_4$-alkoxy or CN, $C_3$-$C_5$-alkenyl, cyclohexyl, $C_7$-$C_9$-phenylalkyl, phenyl or phenyl which is substituted by Cl, $C_1$-$C_4$-alkyl, $C_1$-$C_4$-alkoxy or —COO—($C_1$-$C_4$-alkyl), or $R^{11}$ and $R^1$ together are the group —$CH_2OCH_2$—, $R^{12}$ has one of the meanings given for $R^{11}$ or, together with $R^{11}$, is $C_3$-$C_7$-alkylene which can be interrupted by —O—, —S— or —N($R^{14}$)—, or $R^{12}$, together with $R^2$, is $C_1$-$C_8$-alkylene, $C_7$-$C_{10}$-phenylalkylene, o-xylylene or $C_1$-$C_3$-oxaalkylene or $C_1$-$C_3$-azaalkylene, $R^{13}$ is hydrogen, $C_1$-$C_9$-alkyl, $C_1$-$C_4$-hydroxyalkyl, cyclohexyl, or benzyl, $R^{14}$ is hydrogen, $C_1$-$C_4$-alkyl, $C_1$-$C_4$-hydroxyalkyl, —$CH_2CH_2CN$ or —$CH_2CH_2COO$—($C_1$-$C_4$-alkyl), $R^1$ and $R^2$ independently of one another are $C_1$-$C_8$-alkyl, $C_1$-$C_4$-alkyl which is substituted by OH, $C_1$-$C_4$-alkoxy, CN, —COO—($C_1$-$C_8$-alkyl) or —N($R^{11}$)($R^{12}$), phenyl, chlorophenyl, $R^9$—S—phenyl or $C_7$-$C_9$-phenylalkyl or $R^1$ and $R^2$ together are $C_2$-$C_8$-alkylene, $C_3$-$C_9$-oxaalkylene or $C_3$-$C_9$-azaalkylene, and $R^3$ is a direct bond, $C_1$-$C_6$-alkylene, $C_2$14 $C_6$-oxaalkylene or cyclohexylidene or, together with the two substituents $R^2$ and the two C atoms to which these substituents are attached, forms a cyclopentane, cyclohexane, cyclohexene, endomethylenecyclohexane or endomethylenecyclohexene ring.

Preferred compounds amongst these are those of the formula I in which Ar is a group of the formula IV in which at least one of the radicals $R^4$ to $R^8$ is a group —S—$R^9$.

Compounds of the formula I which are also preferred are those in which Ar is a phenyl radical which is substituted by the group —S—$R^9$, $R^9$ is hydrogen, $C_5$-$C_8$-alkyl, $C_3$-$C_6$-alkenyl, cyclohexyl, benzyl, tolyl or one of the groups —$CH_2CH_2$—OOC—CH=$CH_2$, —$CH_2$—COO—($C_1$-$C_4$-alkyl), —$CH_2CH_2$—COO—($C_1$-$C_4$-alkyl) or

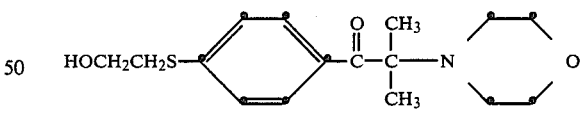

$R^1$ and $R^2$ are $C_1$-$C_4$-alkyl or $R^1$ and $R^2$ together are $C_4$-$C_5$-alkylene and X is a morpholino radical or a radical of the formula —N—($CH_2CH_2OCH_3$)$_2$.

The compound of the formula

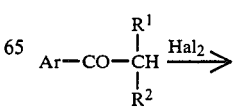

is also novel and also forms the subject of the invention.

The preparation of the compounds of the formula I can be effected analogously to the methods known from European Patent Application, Publication No. 3002, by introducing the amino group into a sulfur-containing aryl alkyl ketone in accordance with the following reaction stages:

$$Ar-CO-\underset{R^2}{\overset{R^1}{\underset{|}{\overset{|}{C}}H}} \xrightarrow{Hal_2} \quad \text{I}$$

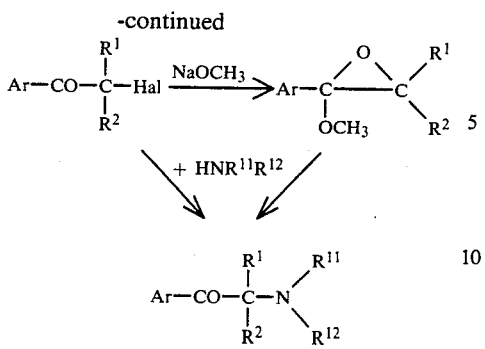

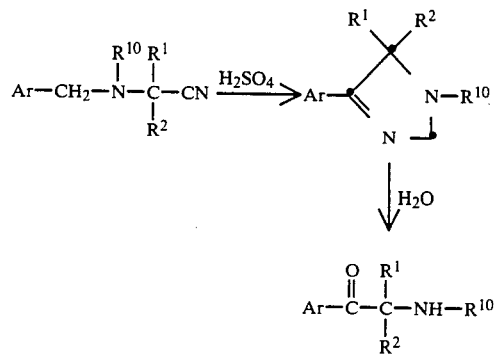

In these formulae Hal is halogen, in particular chlorine or bromine. If, in the last reaction stage here, half a mole of a primary amine, R¹³NH₂, or piperazine or a di-secondary diamine, R¹³NH—(CH₂)ₓNHR¹³ is used, the corresponding compounds of the formula III are obtained.

The compounds of the formula II can be prepared analogously to those of the formula I by using, as the starting material, diketones of the general formula

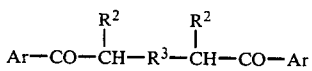

Compounds of the formula I, II or III in which Ar is a phenyl radical which is substituted by a group —S—R⁹ can also be prepared in an alternative manner by first preparing, in accordance with the sequence of reactions indicated above, an aminoketone of the formula I, II or III in which Ar is a phenyl radical which is substituted by halogen, and then replacing the halogen by —S—R⁹. In this case halogen is preferably chlorine and bromine. A replacement of this type can be achieved by means of a reaction with the corresponding mercaptan R⁹SH in the presence of molar amounts of a strong base, or by a reaction with a corresponding alkali metal mercaptide R⁹S-alkali metal. Examples of strong bases which are suitable here are alkali metals or hydroxides, carbonates, amides, hydrides or alcoholates thereof. Examples of these are Na, K, Li, NaOH, KOH, Na₂CO₃, K₂CO₃, NaNH₂, LiNH₂, LiH, NaOCH₃, KOC₄H₉ or NaOC₂H₅. The reaction is preferably carried out in a polar solvent, for example dimethylformamide, dimethylacetamide, ethylene glycol dimethyl ether or dimethyl sulfoxide.

A variant of this route of synthesis is reacting a compound of the formula I, II or III which is substituted by halogen in the aryl radical with an alkali metal hydrosulfide or sulfide, followed by S-alkylating the resulting aryl mercaptan.

A third possible method of preparing compounds of the formula I is reacting α-aminoalkyl nitriles with the corresponding aryllithium compounds:

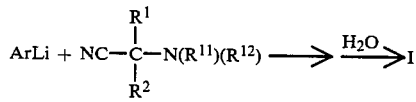

Compounds of the formula II or III can be prepared analogously from the corresponding dinitriles.

Compounds of the formula I in which X is a group —NH₂ or —NHR¹⁰ can alternatively also be prepared from the corresponding benzylaminoacetonitriles by treatment with concentrated sulfuric acid and subsequent hydrolysis, by the method of M. R. Euerby and R. D. Waigh, J. Chem. Res. 1982, 240:

The compounds of the formula I, II or III in which Ar is a phenyl radical substituted by R⁹—SO— can be prepared from the corresponding R⁹—S— compounds in accordance with known methods by selective oxidation, for example by oxidation with per-acids, or in accordance with the method of J. Drabowicz et al., Synthesis 1979, 39, in which the sulfide is treated with bromine and aqueous alkali in a two-phase system.

More precise details relating to the synthesis of compounds of the formula I, II and III can be seen in the preparation examples which follow. In these examples the temperatures are quoted in °C.

EXAMPLE A

Preparation of aminoketone thioethers via the α-halogenoketone thioethers (A₁)

2-Bromo-2-methyl-1-[4-(methylthio)-phenyl]-propan-1-one 369.2 g (1.9 mols) of 2-methyl-1-[4-(methylthio)-phenyl]-propan-1-one are dissolved in 400 ml of carbon tetrachloride. 303.7 g (1.9 mols) of bromine, diluted with 270 ml of carbon tetrachloride, are added dropwise slowly to this solution, with cooling, at room temperature. The dissolved HBr gas is then driven off by blowing with nitrogen. The solution is concentrated and is then reacted further as described below.

(A₂)

3,3-Dimethyl-2-methoxy-2-[4-(methylthio)-phenyl]oxirane 95.1 g (1.76 mols) of sodium methylate are dissolved in 600 ml of methanol, and 437.1 g (1.60 mols) of 2-bromo-2-methyl-1-[4-(methylthio)-phenyl]-propan-1-one, dissolved in 300 ml of methanol, are added dropwise to this solution at reflux temperature. The methanol is then removed by distillation. The residue is poured into ice water, and the mixture is extracted with diethyl ether. The ether solution is washed with water, dried over Na₂SO₄ and concentrated. The crystals obtained are purified by vacuum distillation.

Melting point 62°–64° C.; boiling point 90°–93° C./14 Pa.

(A₃)
2-Methyl-1-[4-(methylthio)-phenyl]-2-morpholinopropan-1-one 151.4 g (0.675 mol) of 3,3-dimethyl-2-methoxy-2-[4-(methylthio)-phenyl]-oxirane (melting point 62°–64° C.) are dissolved in 235.2 g (2.70 mols) of morpholine and the solution is warmed to reflux temperature.

After 15 hours the mixture is cooled and the morpholine is removed by distillation. The residue (melting point 68°–71° C.) is taken up in diethyl ether and the solution is extracted with dilute hydrochloric acid. The hydrochloric acid solution is rendered alkaline and extracted with ether. The ether solution is dried with Na$_2$SO$_4$ and concentrated. The residue can be recrystallised from ethanol.

Melting point 75°–76° C.

C$_{15}$H$_{21}$NO$_2$S (279.40): calculated: C 64.48%; H 7.58%; N 5.01%; O 11.45%; S 11.48%; found: C 64.49% H; 7.51%; N 5.10%; O 11.58%; S 11.51%

Further amine derivatives, listed in Table 1 which follows, are prepared in the same way. In the case of low-boiling amines, the reaction is carried out under pressure. The resulting crude products can be purified by recrystallisation or by chromatography over a silica gel medium-pressure column (migrating agent: mixtures of ethyl acetate and hexane). The structure of all the compounds was confirmed by an H-NMR spectrum.

EXAMPLE B

Preparation of aminoketone thioethers via the halogenoaryl aminoketones (B₁)
2-Chloro-1-(4-chlorophenyl)-2-methylpropan-1-one 182.7 g (1.0 mol) of 1-(4-chlorophenyl)-2-methylpropan-1-one are warmed to 40° and chlorinated with 71 g (1.0 mol) of chlorine gas at 40°–65° in the course of 5 hours. The dissolved HCl gas is then driven off by blowing with nitrogen. The liquid crude product is then reacted further.

(B₂)
2-(4-Chlorophenyl)-3,3-dimethyl-2-methoxyoxirane 57.0 g (1.056 mols) of sodium methylate are dissolved in 360 ml of methanol, and 208.4 g (0.96 mol) of 2-chloro-1-(4-chlorophenyl)-2-methylpropan-1-one are added dropwise to this solution at reflux temperature. The methanol is then removed by distillation. The residue is poured into ice water and the mixture is extracted with diethyl ether. The ether solution is washed with water, dried over Na$_2$SO$_4$ and concentrated. The resulting oil is purified by vacuum distillation.

Boiling point 107° C./1.3 kPa.

C$_{11}$H$_{13}$ClO$_2$ (212.68): calculated: C 62.12%; H 6.16%; Cl 16.67%; found: C 61.89%; H 6.17%; Cl 16.61%

(B₃)
1-(4-Chlorophenyl)-2-methyl-2-morpholinopropan-1-one 85.1 g (0.4 mol) of 2-(4-chlorophenyl)-3,3-dimethyl-2-methoxyoxirane and 139.4 g (1.6 mols) of morpholine are combined and warmed to reflux temperature. After 22 hours the mixture is cooled and morpholine is removed by distillation. The residue is taken up in ether, and the solution is extracted with dilute hydrochloric acid. The hydrochloric acid solution is rendered alkaline and extracted with ether. The ether solution is dried with Na$_2$SO$_4$ and concentrated. The residue is recrystallised from ethanol.

Melting point 73°–75° C.

C$_{14}$H$_{18}$ClNO$_2$ (267.76): calculated: C 62.80%; H 6.77%; N 5.23%; Cl 13.24%; found: C 63.01%; H 6.85%; N 5.33%; Cl 13.14%

(B₄)
1-[4-(2-Hydroxyethylthio)-phenyl]-2-methyl-2-morpholinopropan-1-one 20.1 g (0.075 mol) of 1-(4-chlorophenyl)-2-methyl-2-morpholinopropan-1-one and 6.45 g (0.0825 mol) of mercaptoethanol in 100 ml of dimethylformamide are warmed to 95° C. 20.7 g (0.15 mol) of anhydrous potassium carbonate are then added. The suspension is stirred at 95° C. until the starting compound can no longer be detected. The reaction mixture is cooled and water is poured over it, and the product is taken up in ether. The ether layer is washed with water, dried over Na$_2$SO$_4$ and concentrated. The resulting oil is purified over a drying column, and crystallises after a little time.

Melting point 62°–64° C.

C$_{16}$H$_{23}$NO$_3$S (309.42): calculated: C 62.11%; H 7.49%; N 4.53%; S 10.36%; found: C 62.15%; H 7.59%; N 4.82%; S 10.49%

Further thioether derivatives, listed in Table 1 which follows, are prepared in the same way. In the case of low-boiling mercaptans the reaction is carried out under pressure. The resulting crude products can be purified by recrystallisation or by chromatography over a silica gel medium-pressure column (migrating agent: mixtures of ethyl acetate and hexane). The structure of all the compounds was confirmed by an H-NMR spectrum.

EXAMPLE C

Preparation of mercaptophenyl ketones and S-alkylation thereof (C₁)
1-(4-Mercaptophenyl)-2-methyl-2-morpholinopropan-1-one 451 g of hydrated sodium sulfide (Na$_2$S content 32–38% ≈2 mols) are suspended in 800 ml of N-methyl-2-pyrrolidone and 400 ml of toluene and the mixture is warmed to 130°. Approx. 290 ml of water are removed in a water separator, and the toluene is then removed by distillation. 100 g (0.37 mol) of 1-(4-chlorophenyl)-2-methyl-2-morpholinopropan-1-one are introduced into the warm solution in portions, and the suspension is heated at 140° for 12 hours. After cooling, the pH of the reaction mixture is adjusted to 6 by adding 6N HCl, and the solution is freed from H$_2$S. The solution is then diluted with 1 liter of water and extracted with diethyl ether. The ether extracts are extracted by shaking several times with 20% sodium hydroxide solution, and the combined aqueous alkaline extracts are neutralised with 6N HCl and extracted by shaking with diethyl ether. The ether extracts are dried over MgSO$_4$ and concentrated. The oil which remains is crystallised from cyclohexane. Melting point 68°–69° C. (Compound No. 22).

C$_{14}$H$_{19}$NO$_2$S (265.37): calculated: C 63.37; H 7.22; N 5.28; S 12.08%; found: C 63.42; H 7.31; N 5.40; S 12.05%

(C₂)
1-(4-Allylthiophenyl)-2-methyl-2-morpholinopropan-1-one 10 g (0.38 mol) of 1-(4-mercaptophenyl)-2-methyl-2-morpholinopropan-1-one, 5 g (0.041 mol) of freshly distilled allylbromide and 5.2 g (0.038 mol) of dry potassium carbonate are suspended in 50 ml of acetone and the mixture is heated to reflux temperature for 16 hours. After cooling, the solvent is removed by distillation, water and diethyl ether are added to the residue, and the water phase is extracted with ether. The organic phase is washed with 10% NaOH solution and water, dried over MgSO₄ and concentrated. The oil which remains is distilled in a bulb tube at 180°–200° C./13 Pa. (Compound No. 23).

$C_{17}H_{23}NO_2S$ (305.47): calculated: C 66.84; H 7.60; N 4.59; O 10.48; S 10.50%; found: C 66.92; H 7.64; N 4.63; O 10.60; S 10.52%.

EXAMPLE D

S-Carbalkoxyalkylation

1-[4-(2-Methoxycarbonylethylthio)-phenyl]-2-methyl-2-morpholinopropan-1-one 5 ml of freshly distilled methyl acrylte are added, while cooling with ice, to a solution of 10 g (0.038 mol) of 1-(4-mercaptophenyl)-2-methyl-2-morpholinopropan-1-one and 10 drops of morpholine in 50 ml of dry dioxane. The mixture is stirred for 20 hours at room temperature and diluted with 100 ml of diethyl ether, and the organic phase is washed with saturated NaHCO₃ solution and water. After drying over MgSO₄, the solvent is removed by distillation on a rotary evaporator (compound No. 24).

$C_{18}H_{25}NO_4S$ (351.50): calculated: C 61.51; H 7.17; N 3.98; S 9.12%; found: C 61.63; H 7.30; N 4.05; S 8.94%.

EXAMPLE E

S-Aminomethylation

1-[4-(Dimethylaminomethylthio)-phenyl]-2-morpholinopropan-1-one 7.7 g (0.03 mol) of 1-(4-mercaptophenyl)-2-methyl-2-morpholinopropan-1-one are treated, while being cooled in ice, with 10 ml of a 40% aqueous solution of dimethylamine. After 30 minutes at room temperature the mixture is again cooled in an ice bath, and 3 ml of a 35% aqueous solution of formaldehyde are added dropwise ($\approx$0.038 mol of formaldehyde). The mixture is then stirred at room temperature for 60 minutes and is heated at 50° C. for a further 2 hours. After cooling, 25 ml of diethyl ether are added to the reaction mixture, the phases are separated and the aqueous phase is extracted three times with ether. After the ether solution has been washed with water it is dried over MgSO₄ and evaporated in vacuo, whereupon the crude product is left as an oil (compound No. 34).

EXAMPLE F

Oxidation of the thioethers to give the sulfoxides

A solution of 13 g of m-chloroperbenzoic acid in 50 g of CH₂Cl₂ is added dropwise, at 0° and while stirring, to a solution of 20 g of 2-methyl-1-[4-(methylthio)phenyl]-2-morpholinopropan-1-one in 200 g of methylene chloride. Stirring is continued for a further 2 hours, in the course of which the m-chlorobenzoic acid formed is deposited in the form of a white precipitate. The reaction mixture is poured into ice/1N NaOH, and the organic phase is separated off, dried over Na₂SO₄ and evaporated on a rotary evaporator. The crude 2-methyl-1-[4-(methylsulfenyl)phenyl]-2-morpholinopropan-1-one which remains is recrystallised from ethyl acetate/hexane. Melting point 112°–113° C. (Compound No. 31).

TABLE 1

| Compound No. | Structural formula | Method of preparation | Purification | Physical properties |
|---|---|---|---|---|
| 1 | CH$_3$S-C$_6$H$_4$-CO-C(CH$_3$)$_2$-N(morpholino, O) | A | Crystallisation (ethanol) | Melting point 75–78° |
| 2 | CH$_3$S-C$_6$H$_4$-CO-C(CH$_3$)$_2$-N(piperidino) | A | Crude product | Melting point 53–55° |
| 3 | CH$_3$S-C$_6$H$_4$-CO-C(CH$_3$)$_2$-N(N-methylpiperazino, N—CH$_3$) | A | Crude product | Melting point 100–101° |
| 4 | CH$_3$S-C$_6$H$_4$-CO-C(CH$_3$)$_2$-N(pyrrolidino) | A | Chromatography | liquid |
| 5 | CH$_3$S-C$_6$H$_4$-CO-C(CH$_3$)$_2$-N(CH$_2$CH$_2$OCH$_3$)$_2$ | A | Crude product | liquid |
| 6 | CH$_3$S-C$_6$H$_4$-CO-C(CH$_3$)$_2$-N(C$_4$H$_9$)$_2$ | A | Crude product | liquid |
| 7 | C$_6$H$_5$-S-C$_6$H$_4$-CO-C(CH$_3$)$_2$-N(C$_4$H$_9$)$_2$ | B | Crude product | liquid |
| 8 | C$_6$H$_5$-S-C$_6$H$_4$-CO-C(CH$_3$)$_2$-N(piperidino) | B | Crude product | Melting point 69–72° |

TABLE 1-continued

| Compound No. | Structural formula | Method of preparation | Purification | Physical properties |
|---|---|---|---|---|
| 9 | HO—CH$_2$CH$_2$S—C$_6$H$_4$—CO—C(CH$_3$)$_2$—N(morpholino) | B | Chromatography | Melting point 62–64° |
| 10 | C$_4$H$_9$S—C$_6$H$_4$—CO—C(CH$_3$)$_2$—N(morpholino) | B | Crystallisation (ethanol) | Melting point 88–90° |
| 11 | C$_6$H$_5$—S—C$_6$H$_4$—CO—C(CH$_3$)$_2$—N(N-methylpiperazino) | B | Crystallisation (hexane) | Melting point 79–81° |
| 12 | C$_6$H$_5$—S—C$_6$H$_4$—CO—C(CH$_3$)$_2$—N(CH$_2$CH$_2$OCH$_3$)$_2$ | B | Chromatography | liquid |
| 13 | C$_6$H$_5$—S—C$_6$H$_4$—CO—C(CH$_3$)$_2$—N(morpholino) | B | Crystallisation (ethanol) | Melting point 107–109° |
| 14 | C$_2$H$_5$S—C$_6$H$_4$—CO—C(CH$_3$)$_2$—N(morpholino) | B | Chromatography | Melting point 67–69° |
| 15 | C$_8$H$_{17}$S—C$_6$H$_4$—CO—C(CH$_3$)$_2$—N(morpholino) | B | Chromatography | Melting point 69–71° |
| 16 | CH$_3$S—C$_6$H$_4$—CO—C(C$_2$H$_5$)(C$_4$H$_9$)—N(morpholino) | A | Chromatography | viscous |

TABLE 1-continued

| Compound No. | Structural formula | Method of preparation | Purification | Physical properties |
|---|---|---|---|---|
| 17 | HS—CH$_2$CH$_2$—O—CH$_2$CH$_2$S—C$_6$H$_4$—CO—C(CH$_3$)$_2$—N(morpholino) | B | Chromatography | viscous |
| 18 | CH$_3$S—C$_6$H$_4$—N(morpholino)—C(CH$_3$)$_2$—CO—C$_6$H$_4$—SCH$_3$ | A | Crystallisation (chloroform) | Melting point 188–91° |
| 19 | (morpholino)N—C(CH$_3$)$_2$—CO—C$_6$H$_4$—SCH$_2$CH$_2$—O—CH$_2$CH$_2$S—C$_6$H$_4$—CO—C(CH$_3$)$_2$—N(morpholino) | B | Chromatography | viscous |
| 20 | (morpholino)N—C(CH$_3$)$_2$—CO—C$_6$H$_4$—S—C$_6$H$_4$—CO—C(CH$_3$)$_2$—N(morpholino) | B | Chromatography | Melting point 158–160° |
| 21 | (morpholino)N—C(CH$_3$)$_2$—CO—C$_6$H$_4$—S—CH$_2$COOC$_8$H$_{17}$ | B | Chromatography | viscous |
| 22 | HS—C$_6$H$_4$—CO—C(CH$_3$)$_2$—N(morpholino) | C$_1$ | Crystallisation (cyclohexane) | Melting point 68–69° |
| 23 | CH$_2$=CH—CH$_2$—S—C$_6$H$_4$—CO—C(CH$_3$)$_2$—N(morpholino) | C$_2$ | Distillation | Boiling point 180–200°/13 Pa |
| 24 | CH$_3$—OOC—CH$_2$CH$_2$—S—C$_6$H$_4$—CO—C(CH$_3$)$_2$—N(morpholino) | D | Molecular distillation | Boiling point 180°/0.1 Pa |

TABLE 1-continued

| Compound No. | Structural formula | Method of preparation | Purification | Physical properties |
|---|---|---|---|---|
| 25 | CH₃S-C₆H₃(S)(S)-C₆H₃-CO-C(CH₃)₂-N(morpholine) | A | Crystallisation (ethyl acetate) | Melting point 158–161° |
| 26 | CH₃S-C₆H₄-CO-N(morpholine) | A | Crystallisation (ethanol) | Melting point 93–95° |
| 27 | CH₃S-C₆H₄-CO-C(CH₃)₂-N(CH₃)₂ | A | Crude product | liquid |
| 28 | C₆H₅-CH₂-S-C₆H₄-CO-C(CH₃)₂-N(morpholine) | B | Crude product | Melting point 112–116° |
| 29 | CH₃-C₆H₄-S-C₆H₄-CO-C(CH₃)₂-N(morpholine) | B | Crude product | Melting point 59–63° |
| 30 | CH₃S-C₆H₄-CO-C(CH₃)₂-NH-C₄H₉ | A | Silica gel filtration | liquid |

TABLE 1-continued

| Compound No. | Structural formula | Method of preparation | Purification | Physical properties |
|---|---|---|---|---|
| 31 | CH$_3$-SO-⟨C$_6$H$_4$⟩-CO-C(CH$_3$)$_2$-N(morpholine) | F | Crystallisation (hexane/ethyl acetate) | Melting point 112–113° |
| 32 | ⟨C$_6$H$_5$⟩-S-⟨C$_6$H$_4$⟩-CO-C(CH$_3$)$_2$-N(morpholine) | B | Crystallisation (isopropanol) | Melting point 74–76° |
| 33 | (morpholine)N-C(CH$_3$)$_2$-CO-⟨C$_6$H$_4$⟩-S-S-⟨C$_6$H$_4$⟩-CO-C(CH$_3$)$_2$-N(morpholine) | C$_1$ | Crystallisation | Melting point 122° |
| 34 | (CH$_3$)$_2$N-CH$_2$-S-⟨C$_6$H$_4$⟩-CO-C(CH$_3$)$_2$-N(morpholine) | E | Crude product | liquid |

TABLE 1a

| Compound No. | | C | H | N | S |
|---|---|---|---|---|---|
| 1 | calculated | 64.48 | 7.58 | 5.01 | 11.48% |
|   | found | 64.49 | 7.51 | 5.10 | 11.51% |
| 2 | calculated | 69.27 | 8.36 | 5.04 | 11.56% |
|   | found | 69.14 | 8.42 | 5.21 | 11.18% |
| 3 | calculated | 65.72 | 8.28 | 9.58 | 10.97% |
|   | found | 65.83 | 7.99 | 9.77 | 10.77% |
| 4 | calculated | 68.40 | 8.04 | 5.32 | 12.17% |
|   | found | 68.24 | 8.17 | 5.43 | 12.21% |
| 5 | calculated | 62.74 | 8.36 | 4.30 | 9.85% |
|   | found | 62.89 | 8.32 | 4.56 | 9.78% |
| 6 | calculated | 70.98 | 9.72 | 4.36 | 9.97% |
|   | found | 70.89 | 9.58 | 4.54 | 9.96% |
| 7 | calculated | 75.15 | 8.67 | 3.65 | 8.36% |
|   | found | 75.26 | 8.65 | 3.90 | 7.38% |
| 8 | calculated | 74.30 | 7.42 | 4.13 | 9.44% |
|   | found | 74.34 | 7.44 | 4.20 | 9.21% |
| 9 | calculated | 62.11 | 7.49 | 4.53 | 10.36% |
|   | found | 62.15 | 7.59 | 4.82 | 10.49% |
| 10 | calculated | 67.25 | 8.47 | 4.36 | 9.97% |
|   | found | 67.10 | 8.44 | 4.43 | 9.77% |
| 11 | calculated | 71.15 | 7.39 | 7.90 | 9.04% |
|   | found | 70.99 | 7.15 | 8.19 | 8.68% |
| 12 | calculated | 68.19 | 7.54 | 3.61 | 8.27% |
|   | found | 67.95 | 7.47 | 3.58 | 7.87% |
| 13 | calculated | 70.35 | 6.79 | 4.10 | 9.39% |
|   | found | 70.14 | 6.77 | 3.86 | 9.07% |
| 14 | calculated | 65.50 | 7.90 | 4.78 | 10.93% |
|   | found | 65.65 | 7.72 | 4.83 | 10.71% |
| 15 | calculated | 69.98 | 9.34 | 3.71 | 8.49% |
|   | found | 69.84 | 9.42 | 3.67 | 8.38% |
| 16 | calculated | 68.02 | 8.71 | 4.18 | 9.56% |
|   | found | 68.18 | 8.71 | 4.15 | 9.59% |
| 17 | calculated | 58.50 | 7.36 | 3.79 | 17.35% |
|   | found | 58.63 | 7.32 | 3.86 | 17.40% |
| 18 | calculated | 66.35 | 7.28 | 5.95 | 13.62% |
|   | found | 65.94 | 7.29 | 5.81 | 13.33% |
| 19 | calculated | 63.97 | 7.38 | 4.66 | 10.67% |
|   | found | 62.28 | 7.50 | 4.43 | 12.73% |
| 20 | calculated | 67.71 | 7.31 | 5.64 | 6.46% |
|   | found | 67.75 | 7.45 | 5.75 | 6.32% |
| 21 | calculated | 66.17 | 8.56 | 3.22 | 7.36% |
|   | found | 66.15 | 8.78 | 3.19 | 7.38% |
| 22 | calculated | 63.37 | 7.22 | 5.28 | 12.08% |
|   | found | 63.42 | 7.31 | 5.40 | 12.05% |
| 23 | calculated | 66.84 | 7.60 | 4.59 | 10.50% |
|   | found | 66.92 | 7.64 | 4.63 | 10.52% |
| 24 | calculated | 61.51 | 7.17 | 3.98 | 9.12% |
|   | found | 61.63 | 7.30 | 4.05 | 8.94% |
| 25 | calculated | 64.66 | 5.70 | 3.77 | 17.26% |
|   | found | 64.98 | 5.74 | 4.03 | 17.01% |
| 26 | calculated | 67.67 | 7.88 | 4.38 | 10.03% |
|   | found | 67.76 | 7.77 | 4.55 | 9.94% |
| 27 | calculated | 65.78 | 8.06 | 5.90 | 13.50% |
|   | found | 66.13 | 8.00 | 5.83 | 13.32% |
| 28 | calculated | 70.95 | 7.09 | 3.94 | 9.02% |
|   | found | 70.68 | 7.12 | 4.05 | 8.85% |
| 29 | calculated | 70.95 | 7.09 | 3.94 | 9.02% |
|   | found | 70.83 | 7.03 | 3.81 | 9.00% |
| 30 | calculated | 67.88 | 8.74 | 5.28 | 12.08% |
|   | found | 68.00 | 8.76 | 5.57 | 11.94% |
| 31 | calculated | 60.99 | 7.17 | 4.74 | 10.85% |
|   | found | 61.05 | 7.20 | 4.68 | 10.60% |
| 32 | calculated | 69.12 | 8.41 | 4.03 | 9.22% |
|   | found | 69.04 | 8.64 | 4.18 | 8.99% |
| 33 | calculated | 63.60 | 6.86 | 5.30 | 12.13% |
|   | found | 63.64 | 6.82 | 5.40 | 12.04% |

The pigmented compositions according to the invention contain an olefinically unsaturated, photopolymerisable binder. The binder can consist of one or more unsaturated compounds; preferably it contains two or three unsaturated compounds. In addition, the binder can also contain other film-forming components which are not unsaturated and therefore do not participate in the polymerisation. The unsaturated compounds can contain one or more olefinic double bonds. They can be of a low molecular weight (monomeric) or of a higher molecular weight (oligomeric). Examples of monomers containing one double bond are alkyl acrylates or methacrylates or hydroxyalkyl acrylates or methacrylates, for example methyl, ethyl, butyl, 2-ethylhexyl or 2-hydroxyethyl acrylate, isobornyl acrylate or methyl or ethyl methacrylate. Further examples of the monomers are acrylonitrile, acrylamide, methacrylamide, N-substituted (meth)acrylamides, vinyl esters, such as vinyl acetate, vinyl ethers, such as isobutyl vinyl ether, styrene, alkylstyrenes, halogenostyrenes, N-vinylpyrrolidone, vinyl chloride or vinylidene chloride.

Examples of monomers containing several double bonds are ethylene glycol diacrylate, propylene glycol diacrylate, neopentylglycol diacrylate, hexamethyleneglycol diacrylate or bisphenol A diacrylate, 4,4'-bis-(2-acryloyloxyethoxy)-diphenylpropane, trimethylolpropane triacrylate, pentaerythritol triacrylate or tetraacrylate, vinyl acrylate, divinylbenzene, divinyl succinate, diallyl phthalate, triallyl phosphate, triallyl isocyanurate or tris-(2-acryloyloxyethyl)isocyanurate.

Examples of polyunsaturated compounds of higher molecular weight (oligomeric) are acrylated epoxide resins, acrylated polyethers, acrylated polyurethanes or acrylated polyesters. Further examples of unsaturated oligomers are unsaturated polyester resins, which are in most cases prepared from maleic acid, phthalic acid and one or more diols and which have molecular weights of about 500 to 3,000. Unsaturated oligomers of this type can also be designated prepolymers.

The binders for the photocurable compositions according to the invention can be, for example, a mixture of a monounsaturated and a polyunsaturated monomer.

In most cases, however, two-component mixtures of a prepolymer containing a polyunsaturated monomer, or three-component mixtures which also contain, in addition, a monounsaturated monomer, are used. In this respect the prepolymer primarily determines the properties of the lacquer film; by varying it those skilled in the art can influence the properties of the cured film. The polyunsaturated monomer functions as a crosslinking agent, which makes the lacquer film insoluble. The monounsaturated monomer functions as a reactive diluent by means of which the viscosity is reduced without the necessity of using a solvent.

Two-component and three-component systems of this type based on a prepolymer are used for printing inks as well as for lacquers, photoresists and other coloured, photocurable compositions. One-component systems based on photocurable prepolymers are also frequently used as binders for printing inks.

Unsaturated polyester resins are in most cases used in two-component systems together with a monounsaturated monomer, preferably styrene. Specific one-component systems, for example polymaleimides or polychalcones, are often used for photoresists.

The binder can additionally contain non-photopolymerisable, film-forming components. These can be, for example, polymers which dry physically or solutions thereof in organic solvents, for example nitrocellulose or cellulose acetobutyrate. These can, however, also be chemically curable or heat-curable resins, for example polyisocyanates, polyepoxides or melamine resins. The concomitant use of heat-curable resins is important for use in so-called hybrid systems, which are photopolymerised in a first stage and are crosslinked in a second stage by subsequent heat treatment.

The photocurable compositions according to the invention contain a pigment or a dye. They preferably contain a pigment. The pigment can be an inorganic pigment, for example titanium dioxide (rutile or anatase), iron yellow, iron red, chrome yellow, chrome green, nickel-titanium yellow, ultramarine blue, cobalt blue, cadmium yellow, cadmium red or zinc white. The pigment can be an organic pigment, for example a monoazo or bisazo pigment or a metal complex thereof, a phthalocyanine pigment or a polycyclic pigment, for example a perylene, thioindigo, flavanthrone, quinacridone, tetrachloroisoindolinone or triphenylmethane pigment. The pigment can also be a carbon black or a metal powder, for example aluminium or copper powder. The pigment can also be a mixture of two or more different pigments, such as is customary for achieving specific colour shades.

The pigment can be present in an amount of 5 to 60% by weight, based on the total composition; 10–30% of pigment is present in most cases in printing inks.

Dyes are frequently also used for imparting colour instead of pigments in photoresists or reprographic films. These can be organic dyes belonging to a very wide variety of classes, for example azo dyes, methine dyes, anthraquinone dyes or metal complex dyes. In the concentrations used, these dyes are soluble in the particular binders. The customary concentrations are 0.1 to 20%, preferably 1–5%, by weight, based on the total composition.

Problems similar to those in the radiation curing of coloured compositions can also arise in the radiation curing of uncoloured compositions containing a filler. In these cases too, the photoinitiators described above can be used with success. Examples of compositions of this type are metal primers, priming coats and surface fillers. Examples of fillers in compositions of this type are kaolin, talc, barytes, gypsum, chalk or silicate fillers.

In addition to the three essential components (binder, pigment and photoinitiator), the photopolymerisable composition can contain further constituents which depend especially on the intended field of use. Whereas solvent-free compositions are preferred for most purposes, it can be necessary to add a solvent in order to achieve the viscosity required for the coating. The customary lacquer solvents, which are frequently mixtures of different solvents, are suitable for this purpose. Flow control auxiliaries, thixotropic agents or wetting agents can also be added to achieve a uniform coating. Waxes or other lubricants are frequently added in the case of printing inks.

Although the compositions according to the invention have an excellent stability to storage in the dark, it can be useful for certain purposes, for example for use in tropical countries, to add polymerisation inhibitors. Examples of inhibitors used for this purpose are hydroquinone and derivatives thereof, β-naphthols, sterically hindered phenols, copper compounds, compounds of trivalent phosphorus, phenothiazine, quaternary ammonium compounds or hydroxylamine derivatives.

Conversely, chain transfer agents, such as tertiary amines or thiol compounds, can be added in order to accelerate UV curing or to achieve specific physical properties. The addition of free radical initiators, such as peroxides or other organic per-compounds and benzpinacol or other organic compounds which can be split by heat, can also accelerate photopolymerisation in specific cases.

The compositions according to the invention can also contain a photosensitiser which displaces the spectral sensitivity into specific ranges. This can, for example, be an organic dye, perylene or a derivative of anthracene or thioxanthone. Thioxanthone derivatives, for example alkylthioxanthones or thioxanthonecarboxylic acid esters, in particular, effect a considerable acceleration of photopolymerisation, as sensitisers.

It is preferable to use only one compound of the formula I, II or III as a photoinitiator. However, in special cases it can be advantageous to use a mixture of two such compounds or a mixture with another known photoinitiator. The quantity of photoinitiator required in the photocurable coloured composition is 0.1–20% by weight, preferably 1–6% by weight.

The compositions according to the invention can be used for various purposes. The most important and preferred use is for printing inks. These can be printing inks for offset printing, letterpress printing, gravure printing, screen printing or flexographic printing. The printing inks according to the invention are particularly suitable for offset printing, screen printing and gravure printing.

A second important field of use is their use for paints. Pigmented coatings are used, in particular, as a primer for protecting metals from corrosion, but are also used as coloured top lacquers for decorative purposes on all possible substrates, for example metal, wood, cardboard, plastics or textiles. The use of compositions according to the invention for white lacquers and for black-pigmented metal primers is of particular interest.

Further fields of use are the radiation curing of photoresists, the photo-crosslinking of silver-free films or other fields of photographic reproduction.

In all these uses the photocurable composition is applied in a thin layer to a substrate. If a solvent was present, this is then substantially removed, for example by heating in a drying oven, by passing warm air over the substrate or by infrared irradiation or microwave irradiation. The dried layer is then irradiated with shortwave light, preferably with UV light within the wavelength range of 250–400 nm. Examples of light sources suitable for this purpose are medium-pressure, high-pressure and low-pressure mercury lamps and also super-actinic fluorescent tubes. The radiation curing is preferably carried out in a continuous process, the material to be cured being conveyed past and beneath the source of radiation. The transport speed is decisive for the production rate of the article; it depends on the irradiation time required. For this reason, the acceleration of radiation curing by photoinitiators is an important factor in the production of such articles, and it is one of the advantages of the photoinitiators of the formulae I, II and III that they ensure rapid curing even in a low concentration and even in the case of compositions having a high pigment content.

If a hybrid system is used as the binder, the curing of the film can be carried out in two stages. For example, a prepolymer is produced by radiation polymerisation of the photopolymerisable components, and this is then completely cured by a thermal condensation reaction of the components capable of undergoing condensation. A two-stage procedure of this type can be of interest, for example, for coating or bonding operations, and also in curing relatively thick layers.

Another two-stage process is the combination of electron irradiation and UV irradiation, which is also of interest for fairly thick layers. Whereas the electron radiation effects curing in the depth of the film, the surface is cured by the UV irradiation.

The examples which follow illustrate the properties and applicability of the photocurable compositions according to the invention. In these examples the parts and percentages are by weight.

EXAMPLE 1

A blue printing ink is prepared in accordance with the following formulation:

66 parts of Setalin®AP 560 (urethane acrylate resin made by Synthese, Holland), 11 parts of 4,4'-di-(β-acryloyloxyethoxy)-2,2-diphenylpropane (Ebecryl®150, UCB, Belgium) and 23 parts of Irgalithblau®GLSM (Ciba-Geigy AG, Basel).

The mixture is homogenised on a triple roll mill and ground to a particle size of 5μ.

5 g portions of this printing ink are mixed to form a homogenous mixture with the desired quantity of photoinitiator on a disc grinding machine under a pressure of 180 kg/m², while cooling with water.

Offset prints on strips of special paper measuring 4×20 cm are made with this printing ink, using a test printing apparatus (made by Prüfbau, Federal Republic of Germany). The printing conditions are:

| | |
|---|---|
| coating of printing ink | 2 g/m² |
| applied pressure | 25 kg/cm² |
| printing speed | 2 m/second |

A printing roller with a metal surface (aluminium) is used.

The printed samples are irradiated in a UV irradiation apparatus (QC processor made by RPC, USA) at a lamp output of 80 watt/cm and a distance from the lamp of 11 cm. The irradiation time is varied by varying the transport speed of the samples.

The surface drying of the printing ink is tested by the so-called transfer test immediately after irradiation. This is effected by pressing a white paper onto the printed sample under a pressure of 25 kg/cm². If the paper remains colourless the test is successful. If visible quantities of colour are transferred to the test strips, this is a sign that the surface of the sample is not yet adequately cured.

Table 2 shows the maximum transport speed at which the transfer test was still successful.

The completeness of cure of the printing ink is tested by again preparing offset prints as described above, but using printing rollers having a rubber surface and printing the metal side of aluminium-coated paper strips.

Irradiation is carried out as described above. Immediately after irradiation, the completeness of the cure is tested in an REL apparatus for testing complete curing. In this test, the aluminium cylinder covered with cloth is placed on the printed sample and rotated about its own axis once under a pressure of 220 g/cm² in the course of 10 seconds. If visible damage takes place on the sample in the course of this, the completeness of the curing of the printing ink is inadequate. Table 2 shows the maximum transport speed at which the REL test was still successful.

TABLE 2

| Photoinitiator | | Maximum transport speed (m/minute) | |
|---|---|---|---|
| Compound No. | Quantity (% by weight) | Transfer test (surface curing) | REL test (complete curing) |
| 1 | 6 | >170 | 70 |
| | 3 | 130 | 40 |
| 2 | 6 | 150 | 30 |
| | 3 | 60 | 20 |
| 3 | 6 | 170 | 40 |
| | 3 | 70 | 30 |
| 4 | 6 | 60 | 50 |
| | 3 | 20 | 10 |
| 5 | 6 | >170 | 40 |
| | 3 | 80 | 20 |
| 6 | 6 | 70 | 20 |
| | 3 | 20 | <10 |
| 9 | 6 | >170 | 50 |
| | 3 | 130 | 30 |
| 10 | 6 | 90 | 30 |
| | 3 | 60 | 20 |
| 11 | 6 | 100 | 20 |
| | 3 | 50 | 20 |
| 12 | 6 | 80 | 20 |
| | 3 | 20 | 20 |
| 14 | 6 | 170 | 30 |
| | 3 | 80 | 20 |
| 15 | 6 | 60 | 30 |
| | 3 | 30 | 20 |
| 16 | 6 | >170 | 50 |
| | 3 | 130 | 40 |
| 17 | 6 | >170 | 50 |
| | 3 | 80 | 30 |
| 19 | 6 | >170 | 50 |
| | 3 | 80 | 30 |
| 21 | 6 | 80 | 30 |
| | 3 | 20 | 10 |
| 22 | 6 | >170 | 30 |
| | 3 | 100 | 20 |
| 23 | 6 | 150 | 40 |
| | 3 | 60 | 20 |
| 26 | 6 | >170 | 40 |
| | 3 | 80 | 20 |
| 27 | 6 | 70 | 20 |
| | 3 | 20 | 10 |
| 29 | 6 | >170 | 40 |
| | 3 | 70 | 20 |
| 32 | 6 | >170 | 30 |
| | 3 | 40 | 20 |

EXAMPLE 2

The concomitant use of the thioxanthones as sensitisers.

A white lacquer is prepared in accordance with the following formulation:

17.6 g of Ebecryl®593 (polyester acrylate resin made by UCB, Belgium), 11.8 g of N-vinylpyrrolidone, 19.6 g of titanium dioxide RTC-2 (titanium dioxide made by Tioxide, England), 19.6 g of Sachtolith®HDA (lithopone made by Sachtleben Chemie, West Germany), 11.8 g of trimethylolpropane trisacrylate and 19.6 g of Setalux®UV 2276 (acrylated epoxide resin based on bisphenol A, Kunstharzfabrik Synthese, Holland).

The above components, together with 125 g of glass beads (diameter 4 cm) are ground to a particle size ≦5 μm in a 250 ml glass bottle for at least 24 hours.

The stock paste thus obtained is divided into portions and each portion is mixed with the photoinitiators and photosensitisers (co-initiators) indicated in Table 3, by stirring at 60° C., and the mixtures are ground with glass beads for a further 16 hours.

The white lacquers thus prepared are applied to sheets of glass in a thickness of 30 μm, using a doctor blade. The samples are exposed to light in a single passage in a PPG irradiation apparatus having a lamp output of 80 watt/cm. The speed of passage of the samples through the irradiation apparatus is raised continuously until adequate curing no longer takes place. The maximum speed at which a lacquer film which is still resistant to wiping is formed, is shown in Table 3 as "rate of curing".

The following compounds are used in this test:
PI 1 = compound no. 1 of Table 1
PS 1 = 2-isopropylthioxanthone
PS 2 = 2-dodecylthioxanthone
PS 3 = 2-methyl-6-ethoxycarbonylthioxanthone
PS 4 = compound of the formula

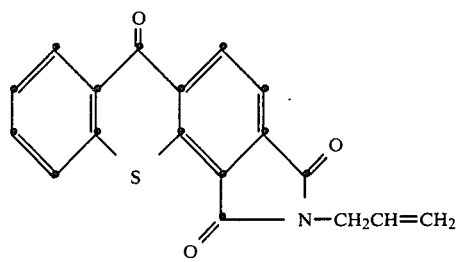

PS 5 = compound of the formula

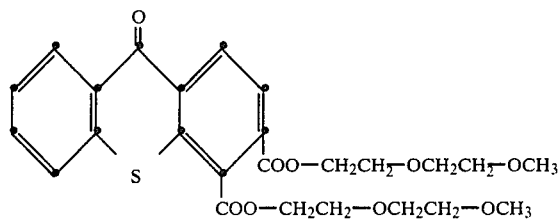

PS 6 = 2-methoxy-6-ethoxycarbonylthioxanthone.

TABLE 3

| Photoinitiator | Co-initiator (sensitiser) | Rate of curing |
| --- | --- | --- |
| 2% of PI 1 | — | 10 m/minute |
| — | 0.5% of PS 3 | 10 m/minute |
| 2% of PI 1 | 0.25% of PS 3 | 70 m/minute |
| 2% of PI 1 | 0.25% of PS 4 | 90 m/minute |
| 2% of PI 1 | 0.25% of PS 5 | 60 m/minute |
| 2% of PI 1 | 0.25% of PS 6 | 70 m/minute |

It can be seen from the table that even small quantities of the sensitiser accelerate the rate of curing considerably.

What is claimed is:

1. A photocurable colored composition comprising: (a) an olefinically unsaturated, photopolymerizable binder, (b) 5-60%, by weight, of a pigment and (c) 0.1-20%, by weight, of a photoinitiator of the formula I

wherein Ar is a phenyl radical which is substituted by the group $-S-R^9$; $R^9$ is hydrogen, $C_1-C_8$-alkyl, $C_3-C_6$-alkenyl, cyclohexyl, benzyl, phenyl, tolyl, $-CH_2CH_2OH$, $-CH_2CH_2-OOC-CH=CH_2$, $-CH_2-COO-(C_1-C_4\text{-alkyl})$, $-CH_2CH_2-COO-(C_1-C_4\text{-alkyl})$,

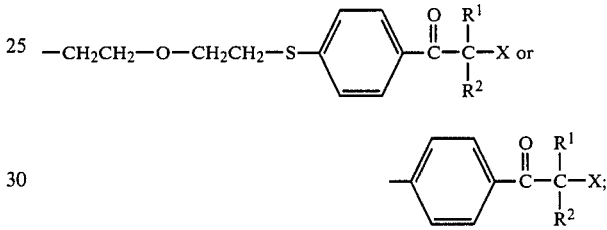

$R^1$ and $R^2$ are $C_1-C_4$-alkyl or $R^1$ and $R^2$ together are $C_4-C_5$-alkylene; and X is a morpholino radical.

2. A composition according to claim 1, wherein the photoinitiator is a compound of the formula I in which Ar is 4-mercaptophenyl, 4-methylthiophenyl or 4-(2-hydroxyethyl)-thiophenyl, $R^1$ and $R^2$ independently of one another are methyl, ethyl or butyl and X is a morpholino group.

3. A printing ink according to claim 1.

4. A composition according to claim 2 wherein said photoinitiator corresponds to the formula

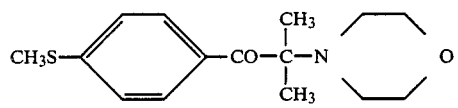

5. A composition according to claim 1, which additionally contains a thioxanthone derivative as a sensitiser.

* * * * *